United States Patent [19]

Coy et al.

[11] Patent Number: 5,112,808
[45] Date of Patent: May 12, 1992

[54] ALKYLATED HORMONE-RELEASING PEPTIDES AND METHOD OF TREATIG MAMMALS THEREWITH

[75] Inventors: David H. Coy, New Orleans; William A. Murphy, Slidell, both of La.

[73] Assignee: American Cyanamid Company, Stamford, Conn.

[21] Appl. No.: 187,402

[22] Filed: May 10, 1988

Related U.S. Application Data

[63] Continuation-in-part of Ser. No. 48,203, May 11, 1987, abandoned.

[51] Int. Cl.$^5$ .................... A61K 37/02; C07K 7/10
[52] U.S. Cl. .................................. 514/12; 514/13; 530/324; 530/325; 930/120; 930/DIG. 822; 930/DIG. 820; 930/DIG. 800
[58] Field of Search ............... 530/324, 325; 514/12, 514/13; 930/120, DIG. 822, DIG. 820, DIG. 800

[56] References Cited

U.S. PATENT DOCUMENTS

| | | | |
|---|---|---|---|
| 4,528,190 | 7/1985 | Vale, Jr. et al. | 530/324 |
| 4,626,523 | 12/1986 | Vale, Jr. et al. | 530/324 |
| 4,689,318 | 8/1987 | Kaiser et al. | 530/324 |
| 4,784,987 | 11/1988 | Rivier et al. | 530/324 |

OTHER PUBLICATIONS

Karken et al., Endocrine Reviews, (1986) pp. 44–66.
Sato et al., Biochemical and Biophysical Res. Communications, vol. 149, No. 2, pp. 531–537 (1987).
Kovacs et al., Life Sciences, vol. 42, pp. 27–35, (1988).
Coy et al., Peptides, vol. 7, pp. 49–52 (1986).
Morrison et al., Organic Chemistry, 3rd ed., pp. 79, 80, 85, 89.

Primary Examiner—Merrell C. Cashion, Jr.
Assistant Examiner—T. D. Wessendorf

[57] ABSTRACT

This invention provides novel growth hormone-releasing peptides and a method for increasing the release and raising the levels of growth hormone in mammals. The invention also provides a method for increasing the growth rate of meat producing animals, treating the symptoms of growth hormone deficiencies in mammals and improving the efficiency of feed utilization by meat producing and dairy animals.

11 Claims, No Drawings

ALKYLATED HORMONE-RELEASING PEPTIDES AND METHOD OF TREATIG MAMMALS THEREWITH

The present invention was supported in part by an award from the National Institute of Health, Grant No. DK 30167. The U.S. Government has certain rights in this invention.

This application is a continuation-in-part of application Ser. No. 07/048,203, filed May 11, 1987, abandoned.

BACKGROUND OF THE INVENTION

During the past decade growth hormone-releasing factors (GRF) of human pancreatic islet tumor origin (hpGRF) have been isolated, characterized and shown to possess growth hormone (GH)-releasing activity in rat anterior pituitary in vitro and in vivo by (1) R. Guillemin, P. Grazeau, P. Bohlen, F. Esch, N. Ling, and W. B. Wehrenberg [Science, 218, 585 (1982)]and (2) J. Spiess, J. Rivier, M. Thorner, and W. Vale [Biochemistry, 21, 6037 (1982)]. A synthetic hp GRF(1-29)-$NH_2$, an amidated fragment of the natural hp GRF, has also been prepared and reported to possess full intrinsic biological activity by Spiess et al. of reference (2).

Additionally, it has been found that an increase in growth hormone (GH)-release in animals can be attained by substituting D-amino acids for L-amino acids of natural hpGRF, especially in the 2 and 3 positions, (Lance et al., Biochemical and Biophysical Research Communications. Vol. 119, No. 1, 1984, pp 265-272: Vale, Jr. et al., U.S. Pat. No. 4,528,190). Likewise, Vale, Jr. et al., have disclosed in the above-mentioned patent that an increase in GH-release is obtained by inserting an N $\alpha$-methyl (or C $\alpha$-methyl-substituted amino acid in positions 1 and 2 of hpGRF. These investigators, however, neither extended the length of the alkyl group beyond methyl on the N-terminus of the hpGRF peptides, nor suggested that such extension would enhance the activity of the hpGRF peptides.

SUMMARY OF THE INVENTION

This invention relates to novel growth hormone-releasing peptides and the use thereof for enhancing the release and increasing the growth hormone levels in mammals.

Unexpectedly, we have now discovered that elongation of the alkyl substituent at the N-terminus and concomitant alkylation of the basic amino acids within the peptide chain, such as lysine in positions 12 and 21, results in substantial increase in potency in eliciting GH-release over that stimulated by the natural hpGRF(1-29)-$NH_2$, hpGRF(1-44)$NH_2$ or [N $\alpha$-MeTyr$^1$]hpGRF(1-29)-$NH_2$.

The present invention thus provides novel mono-and per-alkylated peptides, that are derived by reductive alkylations of GH-releasing peptides through the use of sodium cyanoborohydride and aldehydes or ketones. These peptides of the present invention are extremely potent in stimulating GH-release in warm-blooded animals, including humans.

The novel peptides of this invention are defined as any peptide having from 29 to 44 amino acid residues sequenced as shown in formula A below, and terminated at any amino acid residue function between the 29th and 44th acid residue positions, with the proviso, that the carboxyl moiety of the amino acid residue at the C-terminus is provided with an $R_{17}$ function; wherein $R_{17}$ is OH, $OR_{18}$, $NH_2$ or $NHR_{18}$ and $R_{18}$ is $C_1$–$C_9$ alkyl (straight or branched). $C_3$–$C_6$ cycloalkyl, benzyl, naphthyl, methyl naphthyl or mono-substituted benzyl wherein the substitution is halogen, methoxy, nitro or cyano; with the proviso that when the peptide is the rat GRF, $R_{15}$ is Asn and $R_{16}$ can only be OH, $NH_2$, $OR_{18}$ or Gly; and when Gly is the carboxy-terminus amino acid, the functional group is an acid OH.

The invention also relates to the pharmaceutically acceptable salts of the formula (A) peptides.

The novel peptides of the invention are illustrated by formula A as follows:

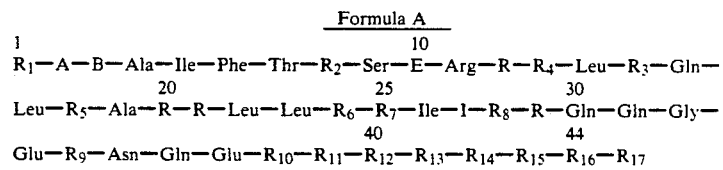

wherein
$R_1$ is $N^\alpha$-$R_{18}$-Tyr, $N^\alpha$-$R_{18}$-His, $N^\alpha$-$R_{18}$-Phe, $N^\alpha$-$R_{18}$-O-Tyr, $N^\alpha$-$R_{18}$-D-His, or $N^\alpha$-$R_{18}$-D-Phe;
A is Ala, D-Ala or N-Me-D-Ala;
B is Asp, D-Asp;
$R_2$ is Asn, D-Asn or Ser;
E is Tyr, D-Tyr;
R is Arg, Lys or $N^\epsilon$-$R_{18}$-Lys;
$R_4$ is Ile or Val;
$R_3$ is Gly, $\alpha$-aminoisobutyric, $\alpha$-aminobutyric, Ala, Gln, Asn, Leu, Ile or Val;
$R_5$ is Ser or tyr;
$R_6$ is His or Gln;
$R_7$ is Glu or Asp;
I is Met, Leu, Nle, Ile, Val, nor Val, Ser, thr, Asn or Gln;
$R_8$ is Ser or Asn;
$R_9$ is Ser or Arg;
$R_{10}$ is Arg or Gln;
$R_{11}$ is Arg or Gly;
$R_{12}$ is Ala or Ser;
$R_{13}$ is Arg or $N^\epsilon$-R-Lys;
$R_{14}$ is Phe, Val or Ala;
$R_{15}$ is Asn or Arg;
$R_{16}$ is Gly or Leu;
$R_{17}$ is OH, $OR_{18}$, $NH_2$ $NHR_{18}$;
$R_{18}$ is $C_1$–$C_9$ alkyl (straight or branched). $C_3$–$C_6$ cycloalkyl, benzyl, naphthyl, methyl naphthyl or mono-substituted benzyl wherein the substitution is halogen, methoxy, nitro or cyano; with the proviso that when the peptide is the rat GRF, $R_{15}$ is Asn and $R_{16}$ can only be OH, $NH_2$, $OR_{18}$ or Gly; and when Gly is the carboxy-terminus amino acid, the functional group is an acid OH; with the further proviso that the formula A peptide can be terminated at any amino acid residue between the 29th and 44th acid residue positions provided that the carboxyl moiety of the amino acid residue at the C-terminus is provided with an $R_{17}$ function, as described above; and the pharmaceutically acceptable salts thereof.

Preferred GRF peptides of the invention are defined in formulas I, III and III as follows:

*Formula I*

$$\begin{array}{c}1\phantom{aaaaaaaaaaaaaaaaaaaaaa}10\\R_1-A-B-Ala-Ile-Phe-Thr-R_2-Ser-E-Arg-R-R_4-Leu-R_3-Gln-\\20\phantom{aaaaaaaaa}25\phantom{aaaaaaaaa}29\\Leu-R_5-Ala-Arg-R-Leu-Leu-R_6-R_7-Ile-I-R_8-Arg-R_{17}\end{array}$$

*Formula II*

$$\begin{array}{c}1\phantom{aaaaaaaaaaaaaaaaaaaaaa}10\\R_1-A-B-Ala-Ile-Phe-Thr-R_2-Ser-E-Arg-R-R_4-Leu-R_3-Gln-\\20\phantom{aaaaaaaaaaaaaaaaaa}30\\Leu-R_5-Ala-R-R-Leu-Leu-R_6-R_7-Ile-I-R_8-R-Gln-Gln-Gly-\\Glu-R_9-Asn-Gln-Glu-R_{10}-R_{11}-R_{12}-R_{13}-R_{14}-R_{15}-R_{16}-R_{17}\end{array}$$

*Formula III*

$$\begin{array}{c}1\phantom{aaaaaaaaaaaaaaaaaaaaaa}10\\R_1-A-B-Ala-Ile-Phe-Thr-R_2-Ser-E-Arg-R-R_4-Leu-R_3-Gln-\\20\phantom{aaaaaaaaaaaaaaaaaa}30\\Leu-R_5-Ala-R-R-Leu-Leu-R_6-R_7-Ile-I-R_8-R-Gln-Gln-Gly-\\40\\Glu-R_9-Asn-Gln-Glu-R_{10}-R_{11}-R_{12}-R_{17}\end{array}$$

Other preferred GRF peptides of this invention are $[N^\alpha\text{-Ethyl-Tyr}^1, Nle^{27}]GRF(1-29)NH_2$ which is $$\begin{array}{c}1\phantom{aaaaaaaaaaaaaaaaaaaa}10\\(N^\alpha\text{-Ethyl})Tyr-Ala-Asp-Ala-Ile-Phe-Thr-Asn-Ser-Tyr-Arg-\\20\\Lys-Val-Leu-Gly-Gln-Leu-Ser-Ala-Arg-Lys-Leu-Leu-Gln-\\29\\Asp-Ile-Nle-Ser-Arg-NH_2;\end{array}$$

$[N^\alpha\text{-Isopropyl-Tyr}^1, Nle^{27}]GRF(1-29)NH_2$ which is $$\begin{array}{c}1\phantom{aaaaaaaaaaaaaaaaaaaa}10\\(N^\alpha\text{-Isopropyl})Tyr-Ala-Asp-Ala-Ile-Phe-Thr-Asn-Ser-Tyr-\\20\\Arg-Lys-Val-Leu-Gly-Gln-Leu-Ser-Ala-Arg-Lys-Leu-Leu-\\29\\Gln-Asp-Ile-Nle-Ser-Arg-NH_2;\end{array}$$

$[N^\alpha\text{-Isopropyl-Tyr}^1]GRF(1-29)N_2$ which is $$\begin{array}{c}1\phantom{aaaaaaaaaaaaaaaaaaaa}10\\(N^\alpha\text{-Isopropyl})Tyr-Ala-Asp-Ala-Ile-Phe-Thr-Asn-Ser-Tyr-\\20\\Arg-Lys-Val-Leu-Gly-Gln-Leu-Ser-Ala-Arg-Lys-Leu-Leu-\\29\\Gln-Asp-Ile-Met-Ser-Arg-NH_2;\end{array}$$

$[N^\alpha\text{-Isopropyl-Tyr}^1, \underline{D}\text{-Ala}^2]GRF(1-29)NH_2$ which is $$\begin{array}{c}1\\(N^\alpha\text{-Isopropyl})Tyr-\underline{D}\text{-Ala}-Asp-Ala-Ile-Phe-Thr-Asn-Ser-\\10\phantom{aaaaaaaaaaaaaaaaa}20\\Tyr-Arg-Lys-Val-Leu-Gly-Gln-Leu-Ser-Ala-Arg-Lys-Leu-\\29\\Leu-Gln-Asp-Ile-Met-Ser-Arg-NH_2;\end{array}$$

$[N^\alpha\text{-Cyclohexyl-Tyr}^1]GRF(1-29)NH_2$ which is $$\begin{array}{c}1\\(N^\alpha\text{-Cyclohexyl})Tyr-Ala-Asp-Ile-Phe-Thr-Asn-Ser-\\10\phantom{aaaaaaaaaaaaaaaaa}20\\Tyr-Arg-Lys-Val-Leu-Gly-Gln-Leu-Ser-Ala-Arg-Lys-Leu-\\29\\Leu-Gln-Asp-Ile-Met-Ser-Arg-NH_2;\end{array}$$

$[N^\alpha\text{-Benzyl-Tyr}^1]GRF(1-29)NH_2$ which is $$\begin{array}{c}1\phantom{aaaaaaaaaaaaaaaaaaaa}10\\(N^\alpha\text{-Benzyl})Tyr-Ala-Asp-Ala-Ile-Phe-Thr-Asn-Ser-Tyr-\\20\\Arg-Lys-Val-Leu-Gly-Gln-Leu-Ser-Ala-Arg-Lys-Leu-Leu-\\29\\Gln-Asp-Ile-Met-Ser-Arg-NH_2;\end{array}$$

$[N^\alpha\text{-Nonyl-Tyr}^1]GRF(1-29)NH_2$ which is 1                                                              10
(N$^\alpha$-Nonyl)Tyr—Ala—Asp—Ala—Ile—Phe—Thr—Asn—Ser—Tyr—Arg—
                                                  20
Lys—Val—Leu—Gly—Gln—Leu—Ser—Ala—Arg—Lys—Leu—Leu—Gln—
                        29
Asp—Ile—Met—Ser—Arg—NH$_2$;

[N$^\alpha$-Isopropyl-Tyr$^1$, N$^\epsilon$-isopropyl-Lys$^{12,21}$]GRF(1-29) NH$_2$ which is
         1
(N$^\alpha$-Isopropyl)Tyr—Ala—Asp—Ala—Ile—Phe—Thr—Asn—Ser—
10
Try—Arg—(N$^\epsilon$-isoproyl)Lys—Val—Leu—Gly—Gln—Leu—Ser—Ala—
20                                                               29
Arg—(N$^\epsilon$-isopropyl)Lys—Leu—Leu—Gln—Asp—Ile—Met—Ser—Arg—
NH$_2$;

[N$^\alpha$-Isopropyl-Try$^1$, N$^\epsilon$-isopropyl-Lys$^{12,21}$]GRF(1-29)OH
which is
              1                                              10
(N$^\alpha$-Isopropyl)Tyr—Ala—Asp—Ala—Ile—Phe—Thr—Asn—Ser—Tyr—
                                                   20
Arg—(N$^\epsilon$-isopropyl)Lys—Val—Leu—Gly—Gln—Leu—Ser—Ala—Arg—
                          29
(N$^\epsilon$-isopropyl)Lys—Leu—Leu—Gln—Asp—Ile—Met—Ser—Arg—OH;

[N$^\alpha$-pentyl-Try$^1$]GRF(1-29)NH$_2$ which is
         1                                                   10
(N$^\alpha$-pentyl)Tyr—Ala—Asp—Ala—Ile—Phe—Thr—Asn—Ser—Tyr—
                                             20
Arg—Lys—Val—Leu—Gly—Gln—Leu—Ser—Ala—Arg—Lys—Leu—Leu—
                     29
Gln—Asp—Ile—Met—Ser—Arg—NH$_2$; and

[N$^\alpha$-Isopropyl-Try$^1$, N$^\epsilon$-isopropyl-Lys$^{12,21}$]GRF(1-29)
NH$_3$ $_{Leu}$—which is
              1                                              10
N$^\alpha$-Isopropyl-Tyr—Ala—Asp—Ala—Ile—Phe—Thr—Asn—Ser—Tyr—
                                                    20
Arg—(N$^\epsilon$-isopropyl)Lys—Val—Leu—Gly—Gln—Leu—Ser—Ala—Arg—
                           29
(N$^\epsilon$-isopropyl)Lys—Leu—Leu—Gln—Asp—Ile—Met—Ser—Arg—NH$_2$;

[N$^\alpha$-Isopropyl-Tyr$^1$, N$^\epsilon$-isopropyl-Lys$^{12,21}$]GRF(1-40)OH
which is
             1                                               10
(N$^\alpha$-Isopropyl)Tyr—Ala—Asp—Ala—Ile—Phe—Thr—Asn—Ser—Tyr—
                                                    20
Arg—(N$^\epsilon$-isopropyl)Lys—Val—Leu—Gly—Gln—Leu—Ser—Ala—Arg—
                           30
(N$^\epsilon$-isopropyl)Lys—Leu—Leu—Gln—Asp—Ile—Met—Ser—Arg—Gln—
Gln—Gly—Glu—Arg—Asn—Gln—Glu—Gln—Gly—Ala—OH

[N$^\alpha$-Isopropyl-Tyr$^1$, N$^\epsilon$-isopropyl-Lys$^{12,21}$]GRF(1-40)OH
which is
             1                                               10
N$^\alpha$-Isopropyl-Tyr—Ala—Asp—Ala—Ile—Phe—Thr—Asn—Ser—Tyr—
                                                    20
Arg—(N$^\epsilon$-Isopropyl)Lys—Val—Leu—Gly—Gln—Leu—Ser—Ala—Arg—
                           30
(N$^\epsilon$-isopropyl)Lys—Leu—Leu—Gln—Asp—Ile—Met—Ser—Arg—Gln—
                                                    40
Gln—Gly—Glu—Arg—Asn—Gln—Gly—Ala—(N$^\epsilon$-isopropyl)Lys—Val—
OH

[N-$^\alpha$-Isopropyl-Tyr$^1$, N$^\epsilon$-isopropyl-Lys$^{12,21}$]GRF(1-40)OH
which is
             1                                               10
(N$^\alpha$-Isopropyl)Tyr—Ala—Asp—Ala—Ile—Phe—Thr—Asn—Ser—Tyr—
                                                    20
Arg—(N$^\epsilon$-isopropyl)Lys—Val—Leu—Gly—Gln—Leu—Ser—Ala—Arg—
                           30
(N$^\epsilon$-isopropyl)Lys—Leu—Leu—Gln—Asp—Ile—Met—Ser—Arg—Gln—
                                            40
Gln—Gly—Glu—Arg—Asn—Gln—Gly—Ala—Arg—Val—OH

[N$^\alpha$-Isopropyl-Tyr$^1$, N$^\epsilon$-isopropyl-Lys$^{12,21}$]GRF(1-40)
NH$_2$ which is
              1                                              10
(N$^\alpha$-Isopropyl)Tyr—Ala—Asp—Ala—Ile—Phe—Thr—Asn—Ser—Tyr—
                                                    20
Arg—(N$^\epsilon$-isopropyl)Lys—Val—leu—Gly—Gln—Leu—Ser—Ala—Arg—

-continued (N⁶-isopropyl)Lys—Leu—Leu—Gln—Asp—Ile—Met—Ser—Arg—Gln—
30
Gln—Gly—Glu—Arg—Asn—Gln—Gly—Ala—(N⁶-isopropyl)Lys—Val—
40
NH₂

[Nᵅ-Isopropyl-Tyr¹, N⁶-isopropyl-Lys¹²,²¹]GRF(1-40)NH₂
which is
1                                                          10
Nᵅ-Isopropyl-Tyr—Ala—Asp—Ala—Ile—Phe—Thr—Asn—Ser—Tyr—
20
Arg—N⁶-isopropyl)Lys—Val—Leu—Gly—Gln—Leu—Ser—Ala—Arg—
30
(N⁶-isopropyl)Lys—Leu—Leu—Gln—Asp—Ile—Met—Ser—Arg—Gln—
Gln—Gly—Glu—Arg—Asn—Gln—Gly—Ala—Arg—Val—NH₂

Other growth hormone releasing peptides of the present invention include the per-alkylated particularly the per-isopropylated, peptides for humans, swine, cattle, goats, sheep and rats. These peptides may be characterized as follows:

HUMAN
[N-isopropyl-Tyr¹, N⁶-isopropyl-Lys-¹²,²¹]GRF(1-44)NH₂
which is
1                                                          10
(N-isopropyl)Tyr—Ala—Asp—Ala—Ile—Phe—Thr—Asn—Ser—Tyr—
20
Arg—(N⁶-isopropyl)Lys—Val—Leu—Gly—Gln—Leu—Ser—Ala—Arg—
30
(N⁶-isopropyl)Lys—Leu—Leu—Gln—Asp—Ile—Met—Ser—Arg—Gln—
40
Gln—Gly—Glu—Arg—Asn—Gln—Glu—Gln—Gly—Ala—Arg—Val—Arg—
44
Leu—NH₂;

PORCINE
[N-isopropyl-Tyr¹, N⁶-isopropyl-Lys-¹²,²¹]GRF(1-42)NH₂
which is
1                                                          10
(N-isopropyl)Tyr—Ala—Asp—Ala—Ile—Phe—Thr—Asn—Ser—Tyr—
20
Arg—(N⁶-isopropyl)Lys—Val—Leu—Gly—Gln—Leu—Ser—Ala—Arg—
30
(N⁶-isopropyl)Lys—Leu—Leu—Gln—Asp—Ile—Met—Ser—Arg—Gln—
40                42
Gln—Gly—Glu—Arg—Asn—Gln—Gly—Ala—Arg—Val—Arg—Leu—NH₂;

BOVINE
[N-isopropyl-Tyr¹, N⁶-isopropyl-Lys¹²,²¹,³⁹]GRF(1-42)-NH₂ which is
1                                                          10
(N-isopropyl)Tyr—Ala—Asp—Ala—Ile—Phe—Thr—Asn—Ser—Tyr—
20
Arg—(N⁶-isopropyl)Lys—Val—Leu—Gly—Gln—Leu—Ser—Ala—Arg—
30
(N⁶-isopropyl)Lys—Leu—Leu—Gln—Asp—Ile—Met—Asn—Arg—Gln—
40
Gln—Gly—Glu—Arg—Asn—Gln—Gly—Ala—(N⁶-isopropyl)Lys—Val—
42
Arg—Leu—NH₂;

CAPRINE
[N-isopropyl-Tyr¹, N⁶-isopropyl-Lys¹²,²¹,⁴¹]GRF(1-44)-NH₂ which is
1                                                          10
(N-isopropyl-Tyr—Ala—Asp—Ala—Ile—Phe—Thr—Asn—Ser—Tyr—
20
Arg—(N⁶-isopropyl)Lys—Val—Leu—Gly—Gln—Leu—Ser—Ala—Arg—
30
(N⁶-isopropyl)Lys—Leu—Leu—Gln—Asp—Ile—Met—Asn—Arg—Gln—
40
Gln—Gly—Glu—Arg—Asn—Gln—Glu—Gln—Gly—Ala—(N⁶-isopropyl)
44
Lys—Val—Arg—Leu—NH₂;

OVINE
[N-isopropyl-Tyr, N⁶-isopropyl-Lys¹²,²¹,⁴¹]GRF(1-44)-NH₂ which is

-continued (N-isopropyl-Tyr—Ala—Asp—Ala—Ile—Phe—Thr—Asn—Ser—Tyr—
                 1                                          10
Arg—(N$^\epsilon$-isopropyl)Lys—Ile—Leu—Gly—Gln—Leu—Ser—Ala—Arg—
                                                         20
(N$^\epsilon$-isopropyl)Lys—Leu—Leu—Gln—Asp—Ile—Met—Asn—Arg—Gln—
                                                         30
Gln—Gly—Glu—Arg—Asn—Gln—Glu—Gln—Ala—(N$^\epsilon$-isopropyl)Lys—
                                                         40
Val—Arg—Leu—NH$_2$;
 43

RAT

[N-isopropyl-His, N$^\epsilon$-isopropyl-Lys$^{21}$]GRF(1-43)OH which is (N-isopropyl-His—Ala—Asp—Ala—Ile—Phe—Thr—Ser—Ser—Tyr—
                 1                                          10
Arg—Arg—Ile—Leu—Gly—Gln—Leu—Tyr—Ala—Arg—(N$^\epsilon$-isopropyl)
                                                         20
Lys—Leu—Leu—His—Glu—Ile—Met—Asn—Arg—Gln—Gln—Gly—Glu—
                                      30
Arg—Asn—Gln—Glu—Gln—Arg—Ser—Arg—Phe—Asn—OH;
       40                    43

BOVINE

[N-isopropyl-Thr—, N$^\epsilon$-isopropyl Lys$^{12,21}$]GRF(1-29)NH$_2$
which is (N-isopropyl)Thr—Ala—Asp—Ala—Ile—Phe—Thr—Asn—Ser—Tyr—
              1                                          10
Arg—(N$^\epsilon$-isopropyl)Lys—Val—Leu—Gly—Gln—Leu—Ser—Ala—Arg—
                                                         20
(N$^\epsilon$-isopropyl)Lys—Leu—Leu—Gln—Asp—Ile—Met—Asn—NH$_2$;
                          25                      28

OVINE

[N-isopropyl-Tyr, N$^\epsilon$-isopropyl-Lys$^{12,21}$]GRF(1-29)NH$_2$
which is (N-isopropyl)Tyr—Ala—Asp—Ala—Ile—Phe—Thr—Asn—Ser—Tyr—
              1                                          10
Arg—(N$^\epsilon$-isopropyl)Lys—Ile—Leu—Gly—Gln—Leu—Ser—Ala—Arg—
                                                         20
(N-isopropyl)Lys—Leu—Leu—Gln—Asp—Ile—Met—Asn—Arg—NH$_2$;
                                                  29

RAT

[N-isopropyl-His, N-isopropyl-Lys$^{21}$]GRF(1-29)NH$_2$ which is (N-isopropyl)His—Ala—Asp—Ala—Ile—Phe—Thr—Ser—Ser—Tyr—
              1                                          10
Arg—Arg—Ile—Leu—Gly—Gln—Leu—Tyr—Ala—Arg—(N-isopropyl)—
                                                         20
Lys—Leu—Leu—His—Glu—Ile—Met—Asn—Arg—NH$_2$; and
                                      29

CAPRINE

[N-isopropyl-Tyr$^1$, N$^\epsilon$-isopropyl-Lys$^{12,21}$]GRF(1-30)OH
which is (N-isopropyl)Tyr—Ala—Asp—Ala—Ile—Phe—Thr—Asn—Ser—Tyr—
              1                                          10
Arg—(N$^\epsilon$-isopropyl)Lys—Val—Leu—Gly—Gln—Leu—Ser—Ala—Arg—
                                                         20
(N$^\epsilon$-isopropyl)Lys—Leu—Leu—Gln—Asp—Ile—Met—Ser—Arg—Gly—
                                                  29
OH;

In keeping with standard nomenclature, the abbreviations used above for chiral amino acid residues and used throughout the present specification and claims are as follows:

Code for L and D-Amino Acids, per IUPAC-IUB Commission on Biochemical Nomenclature: Biochemistry 11, 1726–1732 (1972)

| | |
|---|---|
| His = Histidine | Val = Valine |
| Ser = Serine | Phe = Phenylalanine |
| Asp = Aspartic Acid | Thr = Threonine |
| Ala = Alanine | Asn = Asparagine |
| Tyr = Tyrosine | Gln = Glutamine |
| Arg = Arginine | Met = Methionine |
| Leu = Leucine | Ile = Isoleucine |
| Lys = Lysine | Glu = Glutamic Acid |
| Nle = Norleucine | NorVal = norValine |
| sd,5 D-Ala = sd,5 D-Alanine | |
| sd,5 D-Asp = sd,5 D-Aspartic Acid | |
| sd,5 D-Ser = sd,5 D-Serine | |
| sd,5 D-Tyr = sd,5 D-Tyrosine | |
| sd,5 D-His = sd,5 D-Histidine | |
| sd,5 D-Phe = sd,5 D-Phenylanine | |
| N-Me-sd,5 D-Ala = N-methyl-sd,5 D-alanine | |
| sd,5 D-Asn = sd,5 D-Asparagine | |

Additionally, it should be noted that unless otherwise specified, the amino acid residues that are named herein without the prefix L will, in fact, refer to the naturally occurring absolute configuration L.

Other abbreviations used in the present specification are

```
Fmoc = fluorenylmethyloxycarbonyl
Boc  = t-butyloxycarbonyl
Tos  = p-toluenesulfonyl
hplc = high performance liquid chromatography
tlc  = thin-layer chromatography
TFA  = trifluoroacetic acid
Ac   = acetyl
Z    = benzyloxycarbonyl
```

The term "pharmaceutically acceptable salts" as used herein, refers to non-toxic alkali metal, alkaline earth metal, ammonium, organoammonium and metallic salts commonly used in the pharmaceutical industry. These salts include, but are not limited to, the sodium, potassium, lithium, calcium, magnesium, zinc, ammonium, and trimethylammonium salts which are prepared by methods well known art. The term also includes non-toxic acid addition salts such as hydrochloride, hydrobromide, acetate, phosphate, sulfate, citrate, laurate, stearate, palmoate, and oleate, but are not limited to them. These acid addition salts are also prepared by methods well known in the art.

Further, the term "organoammonium" is defined as a group consisting of a positively charged nitrogen atom joined to from one to four aliphatic groups, each containing from one to 20 carbon atoms. Among the organic ammonium groups which are illustrative for the preparation of the aliphatic ammonium salts of this invention are: monoalkylammonium, dialkylammonium, trialkylammonium, tetraalkylammonium, monoalkenylammonium, dialkenylammonium, trialkenylammonium, monoalkynylammonium, dialkynylammonium, trialkanolammonium, $C_5$–$C_6$ cycloalkylammonium, piperidinium, morpholinium, pyrrolidinium, benzylammonium, and equivalents thereof.

Solid-phase synthesis of the peptides of the present invention can be carried out on a Beckman 990 automatic peptide synthesizer. Preparative HPLC can be performed on a thick-walled glass column (2.5×45 cm) containing Whatman LRP-1 reverse phase packing ($C_{18}$ silica 13-22 μm) pumped with Fluid Metering Company pump and pulse damper. Amino acid analyses can be run on a Beckman 119 CL analyzer and processed with a System AA computing integrator.

Amino acid derivatives utilized in the preparation of the compounds of the present invention are available from several chemical supply houses including: Bachem, Inc., Torrance, Calif., and Chemical Dyanamics, Inc., Plainfield, N.J.

The peptides having configurations shown as formulas A, I, II or III, can be conveniently prepared by standard solid-phase techniques; for example, the C-terminal protected amino acid can be attached to a chloromethyl resin, a hydroxymethyl resin, a benzhydrylamine (BHA) resin or a p-methylbenzylhydrylamine (p-Me-BHA) resin. One such chloromethyl resin is sold under the trade name Bio-Beads SX-1 by Bio Rad Laboratories, Richmond, Calif. The preparation of the hydroxymethyl resin is described by Bodansky et al, *Chem. Ind.* (London) 38. 1597 (1966). The BHA resin has been described by Pietta and Marshall, *Chem. Common.* 650 (1970) and Commercially available from Bachem, Inc., Torrance, Calif.

According to one embodiment of the invention, the peptides of formulas A, (I), (II) and (III), are prepared by means of solid-phase peptide synthesis by standard procedures, although it may also be prepared by treatment of the peptide-resin with ammonia to give the desired side-chain protected amide or with an alkylamine to give a side-chain protected alkylamide or dialkylamide. Further, the asp and glu would also be derivatized residues present as benzyl esters.

The α-amino protecting group is Fmoc for the amino acid in position one, and the side-chain protecting group is Boc instead of Z for the appropriate preceding amino acid, when the chloromethyl or hydroxymethyl resin is used.

Side-chain protection can then be removed in the usual fashion by treatment with HF to give the free peptide amides, alkylamides, or dialkylamides.

In preparing the esters of this invention, the resins used to prepare the acids of formulas A, (I), (II) and (III), where $R_{17}$ is OH, can be employed, and the side-chain protected peptide can be cleaved with a base and appropriate alcohol, i.e., methanol. Side-chain protecting groups can then be removed in the usual fashion by treatment with HF to obtain the desired ester. Alkylation at the N-terminus and concomitant alkylation of the basic amino acids with the peptide chain, such as lysine in the positions 12,21 and 41, can be achieved by removing the BOC protecting groups from the N-Terminus and FMOC groups from the basic amino acids with the resin, subjecting the thus prepared peptide resin to a reduction with an alkali metal cyanoborohydride in the presence of DMF and acetic acid, or in the case of FMOC groups removal with 50% piperidine in DMF, and alkylating the thus prepared resin with the appropriate aldehyde or ketone to yield the desired alkylated GRF resin which can then be cleaved with HF to give the alkylated GRF amine.

FLOW DIAGRAM 1

Preparation [$N^\alpha$-Ethyl-Try$^1$, Nle$^{27}$]GRF(1-29)NH$_2$

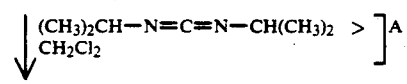

Me—BHA Resin + Boc—Arg($N^\alpha$-Tos)

$$\downarrow \begin{array}{l} (CH_3)_2CH-N=C=N-CH(CH_3)_2 \\ CH_2Cl_2 \end{array} \Bigg\} A$$

Boc—Arg(Tos)—M—BHA Resin $$\downarrow \begin{array}{l} \text{(a) } CH_2Cl_2 \text{ wash} \\ \text{(b) } 33\% \text{ TFA/}CH_2Cl_2, \text{ twice} \\ \text{(c) } CH_2Cl_2 \text{ wash} \\ \text{(d) EtOH wash} \\ \text{(e) } CH_2Cl_2 \text{ wash} \\ \text{(f) } Et_3N/CHCl_3, \text{ twice} \\ \text{(g) } CH_2Cl_2 \text{ wash} \end{array} \Bigg\} B$$

-continued
FLOW DIAGRAM I

Boc—Arg(Tos)—M—BHA Resin

| (1) Boc—Ser(φCH₂), A, B
| (2) Boc—Nle, A, B
| (3) Boc—Ile, A, B
| (4) Boc—Asp(φCH₂), A, B
| (5) Boc—Gln, A, B
| (6) Boc—Leu, A, B
| (7) Boc—Leu, A, B
| (8) Boc—Lys (2-ClφCH₂OCO), A, B
| (9) Boc—Arg(Tos), A, B
| (10) Boc—Ala, A, B
| (11) Boc—Ser(φCH₂), A, B
| (12) Boc—Leu, A, B
| (13) Boc—Gln, A, B
| (14) Boc—Gly, A, B
| (15) Boc—Leu, A, B
| (16) Boc—Val, A, B
| (17) Boc—Lys (2-ClφCH₂OCO), A, B
| (18) Boc—Arg(Tos), A, B
| (19) Boc—Tyr(2-BrφCH₂OCO), A, B

| (20) Boc—Ser(φCH₂), A, B
|      MeOH wash, cycle B
| (21) Boc—Asn, A, B
| (22) Boc—Thr(φCH₂), A, B
| (23) Boc—Phe, A, B
| (24) Boc—Ile, A, B
| (25) Boc—Ala, A, B
| (26) Boc—Asp(φCH₂), A, B
| (27) Boc—Ala, A, B
| (28) Boc—Tyr, A, B
↓

Deblock[Tyr¹, Nle²⁷]GRF(1-29)resin

| (1) DMF/HOAc
| (2) NaBH₃CN
| (3) Alkylate with Aldehyde or
|     ketone
↓

[N$^\alpha$-Ethyl-Tyr¹, Nle²⁷]GRF(1-29)methylbenzhydrylamine resin

| (a) HF, anisole
| (b) Et₂O wash
| (c) AcOH, Sephadex G-50
|     column chromatography
| (d) Lyophilize
| (e) Chromatography:octadecyl-
|     silane silica, 15-20%
|     CH₃CN/H₂O/0.1% TFA/80 psi
| (f) Lyophilize
↓

[N$^\alpha$-Ethyl-Tyr¹, Nle²⁷]GRF(1-29)NH₂

The peptides of the present invention are useful for treatments of symptoms related to growth hormone deficiencies. They are also useful for increasing wool growth, for increasing the rate of growth of meat-producing animals, for improving the carcass quality of meat-producing animals (i.e., more protein and less fat), for improving feed efficiency in meat-producing animals and dairy cows, and for increasing milk production in dairy herds.

As indicated, the compounds of the present invention are effective for increasing the release of growth hormone in mammals, including humans. In practice it is found that said compounds of the invention are effective when administered to mammals in an amount sufficient to provide said treated mammals with from 0.000001 to 0.1 mg/kg of mammalian body weight/day of the formula I or II compounds of the present invention.

In order to facilitate a further understanding of the invention, the following examples are presented primarily for the purpose of illustrating certain more specific details thereof. The invention is not to be deemed limited thereby except as defined in the claims.

EXAMPLE 1

Nle²⁷-GRF(11-29)-methylbenzhydrylamine resin

Methylbenzhydrylamine-polystyrene resin (Vega Biochemicals, Inc.) (3.80 g, 2.0 mmole) in the chloride ion form is placed in the reaction vessel of a Beckman 990B peptide synthesizer programmed to perform the following reaction cycle: (a) methylene chloride; (b) 33% trifluoroacetic acid in methylene chloride (2 times for 1 and 25 min each); (c) methylene chloride; (d) ethanol; (e) methylene chloride; (f) 10% triethylamine in chloroform.

The neutralized resin is stirred with Boc-N$^G$-tosyl-Arg (6 mmole) and diisopropylcarbodiimide (6 mmole) in methylene chloride for 1 hour and the resulting amino acid resin is then cycled through steps (a) to (g) in the above wash program. The following amino acids (6 mmole) are then coupled successively by the same procedure (Gln and Asn in the presence of equimolar 1-hydroxybenzotriazole)):

Boc-O-benzyl-Ser, Boc-Nle, Boc-Ile, Boc-benzyl-Asp-, Boc-Gln, Boc-Leu, Boc-Leu, Boc-N$^e$-2-chlorocarbenzoxy-Lys, Boc-tosyl-Arg, Boc-Ala, Boc-benzyl-Ser, Boc-Leu, Boc-Gln, Boc-Gly, Boc-Leu, Boc-Val, Boc-Cl-Z-Lys, Boc-tosyl-Arg.

After drying, the resin weighs 7.4 g.

EXAMPLE 2

[N$^\alpha$-Ethyl-Tyr¹, Nle²⁷]GRF(1-29)-methylbenzhydrylamine resin

The resin described in Example 1 (2.0 g, 0.5 mmole) is coupled successively with Boc-2-Br-Z-Tyr, Boc-benzyl-Ser, Boc-Asn, Boc-0-benzyl-Thr, Boc-Phe, Boc-Ile-Boc-Ala, Boc-benzyl-Asp, Boc-Ala, and Boc-Tyr. The last Boc group then removed and the resin dried to give 2.65 g of material.

Resin (1,32g, 0.25 mmole) was suspended in DMF/1% acetic acid to which was added NaBH₃CN (3 mmole) followed by acetaldehyde (1 ml). After 1 hour, the resin was completely negative to the Kaiser ninhydrin test.

EXAMPLE 3

[N$^\alpha$-Isopropyl-Tyr¹,Nle²⁷]GRF(1-29)methylbenzhydrylamine resin

The resin described in Example 1 (2.0 g, 0.5 mmole) is coupled successively with Boc-2-Br-Z-Tyr, Boc-benzyl-Ser, Boc-Asn, Boc-0-benzyl-Thr, Boc-Phe, Boc-Ile-Boc-Ala, Boc-benzyl-Asp, Boc-Ala, and Boc-Tyr. This last Boc group was then removed and the resin dried to give 2.65 g of material.

Resin (1.32g, 0.25 mmole) was suspended in DMF/1% acetic acid to which was added NaBH₃CN (3 mmole) followed by acetone (1 ml). After 1 hour, the resin was completely negative to the Kaiser ninhydrin test.

EXAMPLE 4

GRF(3-29)-methylbenzhydrylamine resin

Methylbenzhydrylamine-polystyrene resin (Vega Biochemicals, Inc.) (5.80 g, 3.0 mmole) in the chloride ion form is placed in the reaction vessel of a Beckman 990B peptide synthesizer programmed to perform the following reaction cycle: (a) methylene chloride; (b) 33% trifluoroacetic acid in methylene chloride (2 times for 1 and 25 min each); (c) methylene chloride; (d) ethanol; (e) methylene chloride; (f) 10% triethylamine in chloroform.

The neutralized resin is stirred with Boc-$N^G$-tosyl-Arg (9 mmole) and diisopropylcarbodiimide (9 mmole) in methylene chloride for I hour and the resulting amino acid resin is then cycled through steps (a) to (g) in the above wash program. The following amino acids (9 mmole) are then coupled successively by the same procedure (Gln and Asn in the presence of equimolar 1-hydroxybenzotriazole): Boc-O-benzyl-Ser, Boc-Met, Boc-Ile, Boc-benzyl-Asp, Boc-Gln, Boc-Leu, Boc-Leu, Boc-$N^\epsilon$-2-chlorocarbenzoxy-Lys, Boc-tosyl-Arg, Boc-Ala, Boc-benzyl-Ser, Boc-Leu, Boc-Gln, Boc-Gly, Boc-Leu, Boc-Val, Boc-Cl-Z-Lys, Boc-tosyl-Arg, Boc-2-Br-Z-Tyr, Boc-benzyl-Ser, Boc-Asn, Boc-O-benzyl-Thr, Boc-Phe, Boc-Ile-Boc-Ala, Boc-benzyl-Asp.

The dried resin weighed 18.5 g.

EXAMPLE 5

[$N^\alpha$-Isopropyl-Tyr$^1$,D-Ala$^2$]GRF(1-29)-methylbenzhydrylamine resin

The resin described in Example 4 (1.5 g, 0.5 mmole) is coupled successively with Boc-D-Ala and Boc-Tyr. The last Boc group is then removed and resin was suspended in DMF/1% acetic acid to which was added NaBH$_3$CN (3 mmole) followed by acetone (3 ml). After 18 hours, the resin is completely negative to the Kaiser ninhydrin test.

EXAMPLE 6

[$N^\alpha$-Isopropyl-Tyr$^1$]GRF(1-29)-methylbenzhydrylamine resin

The resin described in Example 4 (1.5 g, 0.5 mmole) is coupled successively with Boc-D-Ala and Boc-Tyr. The last Boc group is then removed and resin was suspended in DMF/1% acetic acid to which was added NaBH$_3$CN (3 mmole) followed by acetone (3 ml). After 18 hours, the resin is completely negative to the Kaiser ninhydrin test.

EXAMPLE 7

[$N^\alpha$-Cyclohexyl-Tyr$^1$]GRF(1-29)-methylbenzhydrylamine resin

The resin described in Example 4 (1.5 g, 0.5 mmole) is coupled successively with Boc-Ala and Boc-Tyr. The last Boc group is then removed and resin was suspended in DMF/1% acetic acid to which was added NaBH$_3$CN (3 mmole) followed by cyclohexanone (3 ml). After 18 hours, the resin is completely negative to the Kaiser ninhydrin test.

EXAMPLE 8

[$N^\alpha$-Benzyl-Tyr$^1$]GRF(1-29)-methylbenzhydrylamine resin

The resin described in Example 4 (1.6 g, 0.5 mmole) is coupled successively with Boc-Ala and Boc-Tyr. The last Boc group is then removed and resin was suspended in DMF/1% acetic acid to which was added NaBH$_3$CN (3 mmole) followed by benzaldehyde (3 ml). After 2 hours, the resin is completely negative to the Kaiser ninhydrin test.

EXAMPLE 9

[$N^\alpha$-5-nonyl-Tyr$^1$]GRF(1-29)-methylbenzhydrylamine resin

The resin described in Example 4 (1.5 g, 0.5 mmole) is coupled successively with Boc-Ala and Boc-Tyr. The last Boc group is then removed and resin was suspended in DMF/1% acetic acid to which was added NaBH$_3$CN (3 mmole) followed by 5-nonanone (3 ml). After 3 days, the resin is very positive to the Kaiser ninhydrin test and is stirred at 50° C. overnight whereupon a negative test is obtained.

EXAMPLE 10

[$N^\alpha$3-pentyl-Tyr$^1$]GRF(1-29)-methylbenzhydrylamine resin

The resin described in Example 4 (1.6 g, 0.5 mmole) is coupled successively with Boc-Ala and Boc-Tyr. The last Boc group is then removed and resin was suspended in DMF/1% acetic acid to which was added NaBH$_3$CN (3 mmole) followed by 3-pentanone (3 ml). After 18 hours, the resin is very positive to the Kaiser ninhydrin test and is stirred at 50° C. for 3 hours whereupon a negative test is obtained.

EXAMPLE 11

[$N^\alpha$-Ethyl-Tyr$^1$,Nle$^{27}$]GRF(1-29)NH$_2$

Peptide resin from Example 2 is mixed with anisole (5 ml) and anhydrous hydrogen fluoride (35 ml) at 0° C. and stirred for 45 min. Excess hydrogen fluoride is evaporated rapidly under a stream of dry nitrogen and free peptide precipitated and washed with ether. The crude peptide is then dissolved in a small volume of 2 M AcOH and eluted on a column (2.5×100 cm) of Sephadex G-50 in the same buffer. Fractions containing a major component by uv absorption and thin layer chromatography are then pooled, evaporated to a small volume and applied to a column (1.5×45 cm) of Vydac octadecylsilane (15 um).

This is eluted with a linear gradient of 15–45% acetonitrile in 0.1% trifluoroacetic acid in water. Fractions are examined by thin layer chromatography and analytical high performance liquid chromatography and pooled to give maximum purity. Repeated lyophilization of the solution from water gives 34 mg of the product as a white, fluffy powder.

The product is found to be homogeneous by hplc and tlc. Amino acid analysis of an acid hydrolysate and fast atom bombardment mass spectrometry confirms the composition of the alkylated.

EXAMPLE 12

[$N^\alpha$-Isopropyl-Tyr$^1$,Nle$^{27}$]GRF(1-29)NH$_2$

Peptide resin from Example 3 is cleaved with HF and purified under the conditions described in Example 11 to give 82 mg of the product as a white, fluffy powder.

The product is found to be homogeneous by hplc and tlc. Amino acid analysis of an acid hydrolysate and fast atom bombardment mass spectrometry confirms the composition of the alkylated.

EXAMPLE 13

[N$^\alpha$-Isopropyl-Tyr$^1$,D-Ala$^2$]GRF(1-29)NH$_2$

Peptide resin from Example 5 is cleaved with HF and purified under the conditions described in Example 11 to give 80 mg of the product as a white, fluffy powder.

The product is found to be homogeneous by hplc and tlc. Amino acid analysis of an acid hydrolysate and fast atom bombardment mass spectrometry confirms the composition of the alkylated.

EXAMPLE 14

[N$^\alpha$-Isopropyl-Tyr$^1$]GRF(1-29)NH$_2$

Peptide resin from Example 6 is cleaved with HF and purified under the conditions described in Example 11 to give 170 mg of the product as a white, fluffy powder.

The product is found to be homogeneous by hplc and tlc. Amino acid analysis of an acid hydrolysate and fast atom bombardment mass spectrometry confirms the composition of the alkylated.

EXAMPLE 15

[N$^\alpha$-Cyclohexyl-Tyr$^1$GRF(1-29)NH$_2$

Peptide resin from Example 7 is cleaved with HF and purified under the conditions described in Example 11 to give 132 mg of the product as a white, fluffy powder.

The product is found to be homogeneous by hplc and tlc. Amino acid analysis of an acid hydrolysate and fast atom bombardment mass spectrometry confirms the composition of the alylated.

EXAMPLE 16

[N$^\alpha$-Benzyl-Tyr$^1$]GRF(1-29)NH$_2$

Peptide resin from Example 8 is cleaved with HF and purified under the conditions described in Example 11 to give 82 mg of the product as a white, fluffy powder.

The product is found to be homogeneous by hplc and tlc. Amino acid analysis of an acid hydrolysate and fast atom bombardment mass spectrometry confirms the composition of the alkylated.

EXAMPLE 17

[N$^\alpha$-5-nonyl-Tyr$^1$]GRF(1-29)NH$_2$

Peptide resin from Example 9 is cleaved with HF and purified under the conditions described in Example 11 to give 68 mg of the product as a white, fluffy powder.

The product is found to be homogeneous by hplc and tlc. Amino acid analysis of an acid hydrolysate and fast atom bombardment mass spectrometry confirms the composition of the alkylated.

EXAMPLE 18

[N$^\alpha$-3-pentyl-Tyr$^1$]GRF(1-29)NH$_2$

Peptide resin from Example 10 is cleaved with HF and purified under the conditions described in Example 11 to give 143 mg of the product as a white, fluffy powder.

The product is found to be homogeneous by hplc and tlc. Amino acid analysis of an acid hydrolysate and fast atom bombardment mass spectrometry confirms the composition of the alkylated.

EXAMPLE 19

[N$^\alpha$-isopropyl-Tyr$^1$, N$^\epsilon$-isopropyl-Lys$^{12,21}$]GRF(1-29)-NH$_2$ GRF(1-29)NH$_2$ (35 mg, 1 umole) is dissolved in DMF/1% AcOH (3 ml) and acetone (0.5 ml). NaBH$_3$CN (4 mg) is then added and the mixture stirred for 4 hours. After removal of the volatile components, the peptide is purified under the conditions described in Example 11 to give 25 mg of the product as a white, fluffy powder.

The product is found to be homogeneous by hplc and tlc. Amino acid analysis of an acid hydrolysate and fast atom bombardment mass spectrometry confirms the composition or the alkylated.

EXAMPLE 20

[N$^\alpha$-isopropyl-Tyr$^1$,N$^\epsilon$-isopropyl-Lys$^{12,21}$]GRF(1-29)OH

GRF(1-29)OH (35 mg, 1 umole) is dissolved in DMF/1% AcOH (3 ml) and acetone (0.5 ml). NaBH$_3$CN (4 mg) is then added and the mixture stirred for 4 hours. After removal of the volatile components, the peptide is purified under the conditions described in Example 11 to give 28 mg of the product as a white, fluffy powder.

The product is found to be homogeneous by hplc and tlc. Amino acid analysis of an acid hydrolysate and fast atom bombardment mass spectrometry confirms the composition of the alkylated.

EXAMPLE 21

Evaluation of peptide effects on growth hormone release in mammals using the rat as the test species In this evaluation, the procedures described by W. A. Murphy et al., Endocrinology 109:491–495 (1980), were employed.

In growth hormone (GH) experiments, male rats (Charles Rivers) were anesthetized with NEMBUTAL ® (6 mg per 100 g body weight) which also served to maintain stimulated plasma GH levels. Exactly 30 minutes after the rats were anesthetized, 0.5 mL of saline or the test peptide in saline was administered as a SC bolus. A 1 mL blood sample was drawn from the jugular vein 15 minutes after the injection of the peptide in saline or at the indicated times in the time course assay (p26). GH levels were determined using NIADDKD rat GH RIA components.

| BIOLOGICAL ACTIVITY OF GRF(1-29)NH$_2$ ANALOGS IN THE PENTOBARBITAL-ANESTHETIZED RAT | | | |
|---|---|---|---|
| TEST SUBSTANCE | DOSE (ug/100 g BW) | PLASMA GH# (ng/ml) | POTENCY* |
| Saline | — | 243 ± 25 (8) | |
| N$^\alpha$MeTry$^1$ | 30 | 1843 ± 196 (6) | 0.42 |
| " | 75 | 2613 ± 418 (6) | (0.30–0.60) |
| Saline | — | 246 ± 36 (7) | |
| N$^\alpha$EtTyr$^1$,Nle$^{27}$ | 4 | 2031 ± 294 (6) | 5.0 |
| " | 10 | 3878 ± 288 (6) | (3.6–7.0) |
| Saline | — | 243 ± 25 (8) | |
| N$^\alpha$iPrTyr$^1$, Nle$^{27}$ | 0.12 | 685 ± 94 (6) | 41 |
| " | 0.30 | 1020 ± 208 (6) | (28–54) |
| Saline | — | 325 ± 52 (9) | |
| N$^\alpha$iPrTyr$^1$ | 0.2 | 1334 ± 394 (6) | ~60 |
| " | 2 | 3250 ± 362 (6) | |
| " | 20 | 3290 ± 241 (6) | |
| N$^\alpha$iPrTyr$^1$, D-Ala$^2$ | 0.2 | 1608 ± 274 (6) | ~70 |

-continued

BIOLOGICAL ACTIVITY OF GRF(1-29)NH₂ ANALOGS IN THE PENTOBARBITAL-ANESTHETIZED RAT

| TEST SUB-STANCE | DOSE (ug/100 g BW) | PLASMA GH# (ng/ml) | POTENCY* |
|---|---|---|---|
| " | 2 | 3836 ± 397 (6) | |
| " | 20 | 3099 ± 485 (6) | |
| Saline | — | 59 ± 9 (9) | |
| N$^α$cyclohexylTyr[1] | 0.2 | 58 ± 21 (6) | ~2 |
| " | 2 | 56 ± 10 (6) | |
| " | 20 | 727 ± 144 (6) | |
| N$^α$benzylTyr[1] | 0.2 | 213 ± 32 (6) | ~50 |
| " | 2 | 606 ± 51 (6) | |
| " | 20 | 1063 ± 140 (6) | |
| Saline | — | 63 ± 8 (9) | |
| N$^α$-5-nonylTyr[1] | 0.2 | 46 ± 4 (6) | <0.5 |
| " | 2 | 85 ± 31 (6) | |
| " | 20 | 104 ± 12 (6) | |
| Saline | — | 91 ± 11 (9) | |
| GRF(1-29)NH₂ | 10 | 222 ± 50 (4) | |
| " | 25 | 622 ± 63 (6) | |
| N$^α$iPrTyr[1], N$^ε$iPrLys[12,21] | 0.08 | 308 ± 24 (6) | |
| N$^α$iPrTyr[1], N$^ε$iPrLys[12,21] | 0.20 | 467 ± 86 (6) | (70-161) |

Two different reference preparations were used for RIA. NIADDK-rGH-RP-1 for assays with higher control values and NIADDK-rGH-RP-2 for assays with lower control values.
*Potencies are calculated using GRF(1-29)NH₂(=1) as standard by 4-point assay (95% CI limits in parentheses) either by comparison to pooled GRF(1-29) NH₂ standards or to standard run in the same bioassay. Potencies without 95% CI's are estimated by single dose comparisons to pooled standard responses.

EXAMPLE 22

Using the method of Example 19, the following perisopropylated peptides are prepared:

1) (N-isopropyl)Tyr-Ala-Asp-Ala-Ile-Phe-Thr-Asn-Ser-Tyr-Arg-(N$^ε$-isopropyl)Lys-Val-Leu-Gly-Gln-Leu-Ser-Ala-Arg-(N$^ε$-isopropyl)Lys-Leu-Leu-Gln-Asp-Ile-Met-Ser-Arg-Gln-Gln-Gly-Glu-Arg-Asn-Gln-Glu-Gln-Gly-Ala-Arg-Val-Arg-Leu-NH₂.

2) (N-isopropyl)Tyr-Ala-Asp-Ala-Ile-Phe-Thr-Asn-Ser-Tyr-Arg-(N$^ε$-isopropyl)Lys-Val-Leu-Gly-Gln-Leu-Ser-Ala-Arg-(N$^ε$-isopropyl)Lys-Leu-Leu-Gln-Asp-Ile-Met-Ser-Arg-Gln-Gln-Gly-Glu-Arg-Asn-Gln-Gly-Ala-Arg-Val-Arg-Leu-NH₂.

3) (N-isopropyl)Tyr-Ala-Asp-Ala-Ile-Phe-Thr-Asn-Ser-Tyr-Arg-(N$^ε$-isopropyl)Lys-Val-Leu-Gly-Gln-Leu-Ser-Ala-Arg-(N$^ε$-isopropyl)Lys-Leu-Leu-Gln-Asp-Ile-Met-Asn-Arg-Gln-Gln-Gly-Glu-Arg-Asn-Gln-Gly-Ala-(N$^ε$-isopropyl)Lys-Val-Arg-Leu-NH₂.

4) (N-isopropyl)Tyr-Ala-Asp-Ala-Ile-Phe-Thr-Asn-Ser-Tyr-Arg-(N$^ε$-isopropyl)Lys-Val-Leu-Gly-Gln-Leu-Ser-Ala-Arg-(N$^ε$-isopropyl)Lys-Leu-Leu-Gln-Asp-Ile-Met-Asn-Arg-Gln-Gln-Gly-Glu-Arg-Asn-Gln-Glu-Gln-Gly-Ala-(N$^ε$-isopropyl)Lys-Val-Arg-Leu-NH₂.

5) (N-isopropyl)Tyr-Ala-Asp-Ala-Ile-Phe-Thr-Asn-Ser-Tyr-Arg-(N$^ε$-isopropyl)Lys-Ile-Leu-Gly-Gln-Leu-Ser-Ala-arg-(N$^ε$-isopropyl)Lys-Leu-Leu-Gln-Asp-Ile-Met-Asn-Arg-Gln-Gln-Gly-Glu-Arg-Asn-Gln-Glu-Gln-Gly-Ala-(N$^ε$-isopropyl)Lys-Val-Arg-Leu-NH₂.

6) (N-isopropyl)His-Ala-Asp-Ile-Phe-Thr-Ser-Ser-Tyr-Arg-Arg-Ile-Leu-Gly-Gln-Leu-Tyr-Ala-Arg-(N$^ε$-isopropyl) Lys-Leu-Leu-His-Glu-Ile-Met-Asn-Arg-Gln-Gln-Gly-Glu-Arg-Asn-Gln-Glu-Gln-Arg-Ser-Arg-Phe-Asn-OH.

7) (N-isopropyl)Thr-Ala-Asp-Ala-Ile-Phe-Thr-Asn-Ser-Tyr-Arg-(N$^ε$-isopropyl)Lys-Val-Leu-Gly-Gln-Leu-Ser-Ala-Arg-(N$^ε$-isopropyl)Lys-Leu-Leu-Gln-Asp-Ile-Met-Asn-Arg-NH₂.

8) (N-isopropyl)His-Ala-Asp-Ala-Ile-Phe-Thr-Asn-Ser-Tyr-Arg-(N$^ε$-isopropyl)Lys-Ile-Leu-Gly-Gln-Leu-Ala-Arg-(N-isopropyl)Lys -Leu-Leu-Gln-Asp-Ile-Met-Asn-Arg-NH₂.

9) (N-isopropyl)His-Ala-Asp-Ala-Ile-Phe-Thr-Ser-Ser-Tyr-Arg-Arg-Ile-Leu-Gly-Gln-Leu-Tyr-Ala-Arg-(N-isopropyl)Lys-Leu-Leu-His-Glu-Ile -Met-Asn-Arg-NH₂.

10) (N-isopropyl)Tyr-Ala-Asp-Ala-Ile-Phe-Thr-Asn-Ser-Tyr-Arg-(N$^ε$-isopropyl)Lys-Val-Leu-Gly-Gln-Leu-Ser-Ala-Arg-(N$^ε$-isopropyl)Lys-Leu-Leu-Gln-Asp-Ile-Met-Ser-Arg-Gln-OH.

EXAMPLE 23

HpGRF(1-29)-Gly-OH

Using the procedure outlined by K. Horiki, et al., in *Chemistry Letters*, 165–168 (1978), Boc-Gly is coupled to the Merrifield chloromethylated resin using KF in DMF at about 60° C. for 24 hours with stirring.

After deblocking and neutralization, the peptide chain is built step-by-step on the resin. Deblocking, neutralization and addition of each amino acid is performed in general accordance with the procedure set forth in detail in Rivier, J. J. *Amer. Chem. Soc.*, 96, 2986–2992 (1974). All solvents that are used are carefully degassed by sparging with an inert gas, e.g. helium or nitrogen, to insure the absence of oxygen that might undesirably oxidize the sulfur of the Met residue.

Deblocking is preferably carried out in accordance with Schedule A which follows:

| SCHEDULE A | |
|---|---|
| Reagent | Mixing time (Min.) |
| 1. 60% TFA/2% ethanedithiol | 10 |
| 2. 60% TFA/2% ethanedithiol | 15 |
| 3. IPA/1% ethanedithiol | 0.5 |
| 4. Et₃N (10%) in CH₂Cl₂ | 0.5 |
| 5. MeOH | 0.5 |
| 6. Et₃N (10%) in CH₂Cl₂ | 0.5 |
| 7. MeOH (twice) | 0.5 |
| 8. CH₂Cl₂ (twice) | 0.5 |

The couplings are preferably carried out as set out in Schedule B which follows:

| SCHEDULE B | |
|---|---|
| Reagent | Mixing time (Min.) |
| 9. DCCI | — |
| 10. Boc-amino acid | 50–90 |
| 11. MeOH (twice) | 0.5 |
| 12. CH₂Cl₂ (twice) | 0.5 |
| 13. Ac₂O (3M) in CH₂Cl₂ | 15.0 |
| 14. CH₂CL₂ | 0.5 |
| 15. MeOH | 0.5 |
| 16. CH₂Cl₂ (twice) | 0.5 |

Briefly, one to two mmol. of BOC-protected amino acid in methylene chloride is used per gram of resin, plus one equivalent of 1.0 molar DCCI in methylene chloride for two hours. When Boc-Arg(TOS) is being coupled, a mixture of 50% DMF and methylene chloride is used. Bzl ether is used as the hydroxyl side-chain protecting group for Ser and Thr. p-Nitrophenyl ester-(ONp) may also be used to activate the carboxyl end of Asn or Gln, and for example, Boc-Asn(ONp) can be coupled overnight using one equivalent of HOBt in a 50% mixture of DMF and methylene chloride, in which case no DCC is added. 2-chloro-benzyloxycarbonyl (Cl-Z is used as the protecting group for the Lys side chain. Tos is used to protect the guanidino group of Arg and the imidazole nitrogen of His, and the Glu or Asp side-chain carboxyl group is protected with OBzl. The following blocked amino acids are then successively coupled: Boc-$N^G$-tosyl-Arg, Boc-O-Bzl-Ser, Boc-Met, Boc-Ile, Boc-benzyl-Asp, Boc-Gln, Boc-Leu, Boc-Leu, Boc-$N^\epsilon$-2-chlorocarbobenzoxy(Cl-Z)-Lys, Boc tosyl-Arg, Boc-Ala, Boc-O-Bzl-Ser, Boc-Gln, Boc-Gly, Boc-Leu, Boc-Val, Boc-Cl-Z-Lys, Boc-tosyl-Arg, Boc-Br-Z-Tyr, Boc-O-Bzl-Ser, Boc-Asn, Boc-O-Bzl-Thr, Boc-Phe, Boc-Ile, Boc-Ala, Boc-Bzl-Asp, Boc-Ala and Boc-Tyr.

In order to cleave and deprotect the protected peptide-resin, it is treated with 1.5 ml. anisole, 0.5 ml. methylethylsulfide and 15 ml. hydrogen fluoride(HF) per gram of peptide-resin, at $-20°$ C. for one-half hour and at $0°$ C. for one-half hour. After elimination of the HF under high vacuum, the resin-peptide remainder is washed alternately with dry diethyl ether and chloroform, and the peptide is then extracted with degassed 2N aqueous acetic acid and separated from the resin by filtration.

The cleaved and deprotected peptide is then dissolved in 0–5% acetic acid and subjected to purification which may include Sephadex G-50 fine gel filtration.

The peptide is then further purified by preparative or semi-preparative HPLC as described in Rivier et al., *Peptides: Structure and Biological Function*, (1979) pp 125–8 and Marki et al *J. Am. Chem. Soc.* 103, 3178 (1981). Cartridges fitting Waters Associates prep LC-500 are packed with 15–20 $\mu$ $C_{18}$ Silica from Vydac (300A). A gradient of $CH_3CN$ in TEAP is generated by a low pressure Eldex gradient maker, as described in Rivier, J., *J. Liq. Chromatography* 1, 343–367 (1978). The chromatographic fractions are carefully monitored by HPLC, and only the fractions showing substantial purity are pooled. Desalting of the purified fractions, independently checked for purity, is achieved using a gradient of $CH_3CN$ in 0.1% TFA. The center cut is then lyophilized to yield the desired peptide, the purity of which can be greater than 98%.

EXAMPLE 24

[$N^\alpha$-Isopropyl-Tyr$^1$, $N^\epsilon$-isopropyl-Lys$^{12,21}$]GRF(1-40)OH hGRF(1-40)OH (5mg, 1 $\mu$mol) is dissolved in DMF/1% AcOH (approx. 1 mL) and acetone (0.1 mL) Na $BH_3CN$ (0.5mg) is than added and the mixture stirred for 5 hours. Excess reagent is quenched by adding 4 mL of 10% HOAc/$H_2O$ followed by 10 mL of $H_2O$. The resulting solution is lyophilized and the crude product is purified by chromatagraphy on a G-10 sephedex column to yield 4.5mg of product as a white fluffy solid.

The product is found to be homogenous by hplc and gives a negative kaiser test. Fast atom bombardment mass spectrometry confirms the composition of the product.

EXAMPLE 25

Evaluation of peptides in vivo in sheep

The purpose of this experiment is to compare the GH releasing activities of several GRF analogs selected for expected high potency and the lack of either a terminal amide or a D-amino acid. The analogs to be compared in wether lambs at 100 ng/kg (IV) are tri-isopropyl-GRF(1-29)-$NH_2$, tri-isopropyl-GRF(1-29)-OH, tri-isopropyl-GRF(1-40)OH, D-ala$^2$, arg$^{12,21}$-GRF (1-29)-OH, D-ala$^2$, arg$^{12,21}$-GRF(1-29)-$NH_2$, GRF(1-40)-OH and GRF(1-29)-$NH_2$ A balanced $8 \times 8$ Latin square design will be used to test the following 8 treatments:

| Group | Treatment | Dose (ng/kg) |
| --- | --- | --- |
| A | Control, vehicle | 0.0 |
| B | GRF(1-29)-$NH_2$ | 100.0 |
| C | GRF(1-40)-OH | 100.0 |
| D | D-ala$^2$, arg$^{12,21}$-GRF(1-29)-$NH_2$ | 100.0 |
| E | D-ala$^2$, arg$^{12,21}$-GRF(1-29)-OH | 100.0 |
| F | tri-isopropyl-GRF(1-29)-$NH_2$ | 100.0 |
| G | tri-isopropyl-GRF(1-29)-OH | 100.0 |
| H | tri-isopropyl-GRF(1-40)-OH | 100.0 |

The diet used in these evaluations is a standard sheep diet (pelleted) and fresh water ad libitum All animals are fed one daily.

The animals are individually identified by numbered ear tags and held in numbered metabolism cages.

Sheep are maintained in individual metabolism cages at all times. Each sheep has previously received an indwelling jugular cannula which is flushed daily with heparinized (400–800 IU/ml) sterile saline to help maintain potency.

All compounds are solubilized at 5 ug/ml in sterile saline containing 1% Tween 80 and injected intravenously at 100 ng/kg. Control lambs receive equal volumes of the vehicle only. The drugs are prepared each day just prior to injection to minimize sticking to the vials.

Blood is collected in heparinized tubes at 15 minute intervals for one hour prior to and for two hours after the treatments are administered. Plasma samples are removed by centrifugation and frozen.

Body weights of each animal is taken at the start of the experiment and once during treatment.

Blood samples are taken from each animal at 15 minute intervals for 3 hours each day during the 8 day trial period. The samples are analyzed for plasma growth hormone (ng/ml). Data obtained are reported below as near values obtained for each treatment.

EFFECTS OF VARIOUS GRF ANALOGS ON PLASMA GH LEVELS IN LAMBS INJECTED INTRAVENOUSLY AT 100 NG/KG.

| GRF Analog | Plasma GH (ng/ml)$^a$ | | |
| --- | --- | --- | --- |
| | Pre-inj Mean$^b$ | Post-inj Mean$^c$ | Peak |
| Control | 8.4 | 8.7 | 12.2 |
| GRF(1-29)-$NH_2$ | 8.9 | 11.3 | 23.2 |
| GRF(1-40)-OH | 9.4 | 25.5 | 92.3 |
| D-ala$^2$,arg$^{12,21}$-GRF(1-29)-$NH_2$ | 8.9 | 19.1 | 62.8 |
| D-ala$^2$,arg$^{12,21}$-GRF(1-29)-OH | 8.5 | 19.4 | 65.0 |
| tri-isopropyl-GRF(1-29)-$NH_2$ | 9.7 | 22.0 | 71.9 |
| tri-isopropyl-GRF(1-29)-OH | 9.4 | 17.2 | 53.1 |
| tri-isopropyl-GRF(1-40)-OH | 9.5 | 34.0 | 108.6 |

$^a$Means within columns without a common superscript are different (P < .05).
$^b$Means of 5 samples/animal from 8 animals.
$^c$Means of 8 samples/animal from 8 animals.

What is claimed is:

1. A peptide having a formula:
$R_1$-A-Asp-Ala-Ile-Phe-Thr-Asn-Ser-Tyr-Arg-R-Val-Leu-Gly-Gln-Leu-Ser-Ala-R-R-Leu-Leu-Gln-Asp-Ile-I-Ser-R-$NH_2$,
wherein $R_1$ is $N^\alpha$-$R_{18}$-Tyr or $N^\alpha$-$R_{18}$-D-Tyr;
A is Ala or D-Ala;
R is Arg or Lys;
I is Met or Nle;
$R_{18}$ is straight or branched $C_2$-$C_7$ alkyl, cyclohexyl or benzyl; or a pharmaceutically acceptable salt thereof.

2. A peptide according to claim 1, $$\overset{1}{(N^\alpha\text{-Ethyl})\text{Tyr}}-\text{Ala}-\text{Asp}-\text{Ala}-\text{Ile}-\text{Phe}-\text{Thr}-\text{Asn}-\text{Ser}-\overset{10}{\text{Tyr}}-\text{Arg}-$$
$$\text{Lys}-\text{Val}-\text{Leu}-\text{Gly}-\text{Gln}-\text{Leu}-\text{Ser}-\text{Ala}-\overset{20}{\text{Arg}}-\text{Lys}-\text{Leu}-\text{Leu}-\text{Gln}-$$
$$\text{Asp}-\text{Ile}-\text{Nle}-\text{Ser}-\overset{29}{\text{Arg}}-\text{NH}_2.$$

3. A peptide according to claim 1, $$\overset{1}{(N^\alpha\text{-Isopropyl})\text{Tyr}}-\text{Ala}-\text{Asp}-\text{Ala}-\text{Ile}-\text{Phe}-\text{Thr}-\text{Asn}-\text{Ser}-\overset{10}{\text{Tyr}}-$$
$$\text{Arg}-\text{Lys}-\text{Val}-\text{Leu}-\text{Gly}-\text{Gln}-\text{Leu}-\text{Ser}-\text{Ala}-\overset{20}{\text{Arg}}-\text{Lys}-\text{Leu}-\text{Leu}-$$
$$\text{Gln}-\text{Asp}-\text{Ile}-\text{Nle}-\text{Ser}-\overset{29}{\text{Arg}}-\text{NH}_2.$$

4. A peptide according to claim 1, $$\overset{1}{(N^\alpha\text{-Isopropyl})\text{Try}}-\text{Ala}-\text{Asp}-\text{Ala}-\text{Ile}-\text{Phe}-\text{Thr}-\text{Asn}-\text{Ser}-\overset{10}{\text{Tyr}}-$$
$$\text{Arg}-\text{Lys}-\text{Val}-\text{Leu}-\text{Gly}-\text{Gln}-\text{Leu}-\text{Ser}-\text{Ala}-\overset{20}{\text{Arg}}-\text{Lys}-\text{Leu}-\text{Leu}-$$
$$\text{Gln}-\text{Asp}-\text{Ile}-\text{Met}-\text{Ser}-\overset{29}{\text{Arg}}-\text{NH}_2.$$

5. A peptide according to claim 1, $$\overset{1}{(N^\alpha\text{-Isopropyl})\text{Tyr}}-\underline{\text{D}}-\text{Ala}-\text{Asp}-\text{Ala}-\text{Ile}-\text{Phe}-\text{Thr}-\text{Asn}-\text{Ser}-$$
$$\overset{10}{\text{Tyr}}-\text{Arg}-\text{Lys}-\text{Val}-\text{Leu}-\text{Gly}-\text{Gln}-\text{Leu}-\text{Ser}-\text{Ala}-\overset{20}{\text{Arg}}-\text{Lys}-\text{Leu}-$$
$$\text{Leu}-\text{Gln}-\text{Asp}-\text{Ile}-\text{Met}-\text{Ser}-\overset{29}{\text{Arg}}-\text{NH}_2.$$

6. A peptide according to claim 1, $$\overset{1}{(N^\alpha\text{-Cyclohexyl})\text{Tyr}}-\text{Ala}-\text{Asp}-\text{Ala}-\text{Ile}-\text{Phe}-\text{Thr}-\text{Asn}-\text{Ser}-$$
$$\overset{10}{\text{Tyr}}-\text{Arg}-\text{Lys}-\text{Val}-\text{Leu}-\text{Gly}-\text{Gln}-\text{Leu}-\text{Ser}-\text{Ala}-\overset{20}{\text{Arg}}-\text{Lys}-\text{Leu}-$$
$$\text{Leu}-\text{Gln}-\text{Asp}-\text{Ile}-\text{Met}-\text{Ser}-\overset{29}{\text{Arg}}-\text{NH}_2.$$

7. A peptide according to claim 1, $$\overset{1}{(N^\alpha\text{-Benzyl})\text{Tyr}}-\text{Ala}-\text{Asp}-\text{Ala}-\text{Ile}-\text{Phe}-\text{Thr}-\text{Asn}-\text{Ser}-\overset{10}{\text{Tyr}}-$$
$$\text{Arg}-\text{Lys}-\text{Val}-\text{Leu}-\text{Gly}-\text{Gln}-\text{Leu}-\text{Ser}-\text{Ala}-\overset{20}{\text{Arg}}-\text{Lys}-\text{Leu}-\text{Leu}-$$
$$\text{Gln}-\text{Asp}-\text{Ile}-\text{Met}-\text{Ser}-\overset{29}{\text{Arg}}-\text{NH}_2.$$

8. A peptide according to claim 1, $$\overset{1}{(N^\alpha\text{-pentyl})\text{Tyr}}-\text{Ala}-\text{Asp}-\text{Ala}-\text{Ile}-\text{Phe}-\text{Thr}-\text{Asn}-\text{Ser}-\overset{10}{\text{Tyr}}-$$
$$\text{Arg}-\text{Lys}-\text{Val}-\text{Leu}-\text{Gly}-\text{Gln}-\text{Leu}-\text{Ser}-\text{Ala}-\overset{20}{\text{Arg}}-\text{Lys}-\text{Leu}-\text{Leu}-$$
$$\text{Gln}-\text{Asp}-\text{Ile}-\text{Met}-\text{Ser}-\overset{29}{\text{Arg}}-\text{NH}_2.$$

9. A method for increasing the release of growth hormone in mammals, said method comprising administering to said mammals from 0.000001 to 0.1 mg/kg of mammalian body weight per day of a peptide having the formula of the peptide of claim 1.

10. The method according to claim 9, wherein said peptide is:
[$N^\alpha$-Ethyl-Tyr$^1$, Nle$^{27}$]GRF(1-29)NH$_2$;
[$N^\alpha$-Pentyl-Tyr$^1$]GRF(1-29)NH$_2$;
[$N^\alpha$-Benzyl-Tyr$^1$]GRF(1-29)NH$_2$;
[$N^\alpha$-Cyclohexyl-Tyr$^1$]GRF(1-29)NH$_2$;
[$N^\alpha$-Isopropyl-Tyr$^1$]GRF(1-29)NH$_2$;
[$N^\alpha$-Isopropyl-Tyr$^1$, D-Ala$^2$]GRF(1-29)NH$_2$ or
[$N^\alpha$-Isopropyl-Tyr$^1$, Nle$^{27}$]GRF(1-29)NH$_2$.

11. A method of stimulating the release of growth hormone in an animal, which comprises administering to said animal an effective amount of the peptide of claim 1 or the salt thereof, pharmaceutically acceptable.

* * * * *